USOO5601998A

United States Patent [19]
Mach et al.

[11] Patent Number: 5,601,998
[45] Date of Patent: Feb. 11, 1997

[54] CULTURE MEDIUM AND DEVICE FOR DETECTION AND ENUMERATION OF ENTEROBACTERIACEAE

[76] Inventors: Patrick A. Mach; Peter D. Wickert; Carl A. Adams, all of P.O. Box 33427, St. Paul, Minn. 55133-3427

[21] Appl. No.: 292,784

[22] Filed: Aug. 18, 1994

[51] Int. Cl.[6] .............................. C12Q 1/04; C12Q 1/00; C12Q 1/02; C12Q 1/10
[52] U.S. Cl. .................. 435/34; 435/4; 435/29; 435/23; 435/12; 435/848; 435/849; 435/38; 436/74; 436/63; 422/55; 422/57; 422/68.1
[58] Field of Search .............................. 435/34, 4, 29, 435/12, 805, 23, 848, 849, 38; 436/501, 74, 63; 422/55, 57, 68.1

[56] References Cited

U.S. PATENT DOCUMENTS

| | | | |
|---|---|---|---|
| 3,359,180 | 12/1967 | Evans et al. | 435/34 |
| 3,960,658 | 6/1976 | Avakian et al. | 435/34 |
| 4,010,078 | 3/1977 | Taylor | 435/34 |
| 4,308,346 | 12/1981 | Niwano | 435/34 |
| 4,308,347 | 12/1981 | Forrer et al. | 435/34 |
| 4,335,205 | 6/1982 | Greenwood | 435/34 |
| 4,416,984 | 11/1983 | Wheeler, Jr. | 435/31 |
| 4,544,637 | 10/1985 | Keggins et al. | 435/34 |
| 4,565,783 | 1/1986 | Hansen et al. | 435/299 |
| 4,748,113 | 5/1988 | Marshall | 435/12 |
| 4,775,621 | 10/1988 | Berkhoff et al. | 435/38 |
| 4,906,565 | 3/1990 | Vossen | 435/15 |
| 5,073,488 | 12/1991 | Matner et al. | 435/31 |
| 5,089,413 | 2/1992 | Nelson et al. | 435/254 |
| 5,094,955 | 3/1992 | Calandra et al. | 435/34 |
| 5,232,838 | 8/1993 | Nelson et al. | 435/30 |
| 5,266,486 | 11/1993 | Fraatz et al. | 435/35 |
| 5,292,644 | 3/1994 | Berg | 435/29 |
| 5,364,766 | 11/1994 | Mach et al. | 435/34 |

FOREIGN PATENT DOCUMENTS

| | | | |
|---|---|---|---|
| 0161481 | 4/1988 | European Pat. Off. | C12Q 1/04 |
| WO82/02563 | 8/1982 | WIPO | C12Q 1/24 |

OTHER PUBLICATIONS

Sokolova et al, Chem Abstract, vol. 109:51287, 1987.
Costilow, "Biophysical Factors in Growth", Manual for Methods for General Bacteriology, Chapter 6, 1981.
Standridge et al., "Underestimation of Total–Coliform Counts by the Membrane Filter Verification Procedure", *Applied and Environmental Microbiology*, vol. 44, No. 4, pp. 1001–1003, Oct. 1982.
Barth, Chemical Abstract, vol. 99, p. 341, Ref. #118862e, 1983.
The Merck Index, Tenth Edition, p. 930 and pp. 1044–1045, 1983.
LeChevallier et al., "New Medium for Improved Recovery of Coliform Bacteria from Drinking Water", *Applied and Environmental Microbiology*, vol. 45, No. 2, pp. 484–492, Feb. 1983.
Abstract, Derwent Publications Ltd., AN 92–380047 & SU A 1,703,695, Jan. 7, 1992.
Martins et al., Biological Abstracts, vol. 92, No. 12, Ref. #141153, Water Res 25(10), 1279–1284, 1991.
Pettibone, *Letters in Applied Microbiology*, vol. 15, pp. 190–192, 1992.

(List continued on next page.)

*Primary Examiner*—John Kight
*Assistant Examiner*—Louise N. Leary

[57] ABSTRACT

This invention generally relates to products and processes used to determine the presence of Enterobacteriaceae in a sample and particularly relates to a bacterial culture medium which may be used in products and processes to allow early detection and enumeration of Enterobacteriaceae in a sample. The bacterial culture medium which facilitates the early detection and enumeration of Enterobacteriaceae contains a selected amount of glucose, pH indicator and buffer which prevent diffusion of colored indicator zones associated with growing bacteria in the medium.

13 Claims, 1 Drawing Sheet

OTHER PUBLICATIONS

Microorganisms in Foods, "Their Significance and methods of Enumeration", *University of Toronto Press*, Second Edition.

U.S. patent application Ser. No. 08/168,681, Krejcarek et al., filed Dec. 17, 1993, entitled "Automated Incubating and Imaging System for a Disposable Microorganism Culturing Device".

U.S. patent application Ser. No. 08/240,846, Graessle et al., filed May 11, 1994, entitled "Cassette for Disposable Microorganism Culturing Media and Automated Scanning Sysem".

U.S. patent application Ser. No. 08/272,996, Floeder et al., filed Jul. 14, 1994, entitled "A Technique To Count Objects in a Scanned Image".

Gerasimenko et al., *Chemical Abstracts*, vol. 77, p. 398, Ref. #18158g, 1972.

BBL Manual of Products and Laboratory Procedures, Fifth Edition, 1973, pp. 131–132.

Moats et al., "Observations on Brilliant Green Agar with an $H_2S$ Indicator", *Applied and Environmental Microbiology*, vol. 31, No. 3, pp. 380–384, Mar. 1976.

Lin, "Membrane Filter Method for Recovery of Fecal Coliforms in Chlorinated Sewage Effluents", *Applied and Environmental Microbiology*, vol. 32, No. 4, pp. 547–552, Oct. 1976.

Mossel, et al., "Optimalisation of a MacConkey–type medium for the enumeration of Enterobacteriaceae", Laboratory Practice, pp. 1049–1050, 1978.

FIG.1

CULTURE MEDIUM AND DEVICE FOR DETECTION AND ENUMERATION OF ENTEROBACTERIACEAE

This invention generally relates to products and processes used to detect and enumerate Enterobacteriaceae in a sample and particularly relates to a thin film, dry culture medium device and a method of using this thin film device which may be used to detect and enumerate Enterobacteriaceae in food samples.

BACKGROUND

The family EnterobacteriaCeae include bacteria that are characterized as small, gram-negative, oxidase negative, non-sporulating rods that are capable of fermenting glucose. These microorganisms are found in habitats such as the intestinal tract, soil, water, vegetables and other food sources such as meats and dairy products. Some members of this family are known human pathogens such as bacteria of the genus escherichia, salmonella, shigella and enterobacter.

Classical methods for determining the presence and number of Enterobacteriaceae in a sample are time consuming, tedious and labor intensive. Typically, a technician must prepare reagents and nutrients, mix the nutrients with agar, heat the mixture, pour the mixture into a petri dish, obtain a test sample, dilute the test sample, add an aliquot of the diluted sample to the agar, allow the agar to gel, incubate the inoculated plate for 24–48 hours and finally count the number of growing bacterial colonies in the petri dish. If needed, confirmatory tests may also need to be performed in order to particularly identify specific bacteria. Products and processes which reduce preparation time and allow reliable detection and colony count of Enterobactefi.aceae in a sample would clearly be welcomed by those working in this field.

One example of a product which greatly simplifies the above preparation time is thin film, dry culture medium devices for growing microorganisms that are described in U.S. Pat. No. 4,565,783 to Hansen et at., U.S. Pat. No. 5,089,413 to Nelson et at. and U.S. Pat. No. 5,232,838 to Nelson et al. In a representative thin film device, a cold-water soluble dry powder containing a gelling agent, microbial growth nutrients and minerals and an indicator dye is coated on a waterproof substrate. The waterproof substrate is covered with a foam spacer which provides an inoculation area. A transparent, read-through cover sheet that is coated on an inner surface with an acrylate adhesive containing an indicating dye and powdered gelling agent is attached to the foam spacer.

When the device is used, a predetermined amount of an aqueous sample is typically placed in contact with the coated substrate in an area defined by the foam spacer and the cover sheet is placed over the sample and substrate. The aqueous sample hydrates the soluble dry powder which then forms a gelled medium capable of sustaining microbial growth. During the growth period, the indicator dye adhered to the cover sheet reacts in the presence of viable microorganisms to give a detectable response that allows visualization of bacterial colonies which are grown on the culture device. Different types of thin film dry culture medium devices are commercially available as PETRIFILM thin film, dry culture medium plates from 3M, St. Paul, Minn.

The thin film, dry culture medium devices are much simpler to use than conventional gelled agar mediumpetri/dish systems because there is no need for the user to heat and mix the growth medium, agar and other reagents and then add the mixture to petri dishes or pour plates. In addition, the devices of Hansen et al. are compact and easily disposed of and therefore are easier and safer to use.

For example, a culture medium which may be used in a thin film plate in order to provide a rapid count of coliform bacteria is reported in U.S. application Ser. No. 08/062,311, filed May 5, 1993, now U.S. Pat. No. 5,364,766 to Mach et al. In this document, an aliquot of the sample containing coliform bacteria is added to a culture medium comprising tryptose, lactose, sodium chloride, bile salts, and an excess amount of a pH indicator, phenol red, which provides a high concentration of phenol red in close proximity to the bacteria growing in the medium. The use of the reported medium and high concentration of phenol red allow the detection and count of coliform bacteria in less than 24 hours. The reported medium, however, is hampered by diffusion of the pH indicator through the medium as the device is incubated. More specifically, the presence of coliform bacteria is initially detected by a visual color change of the phenol red indicator from a red to a yellow color in a zone around the growing microbial colony that is caused by the production of organic acids by the growing microorganisms. As the growing bacteria continue to produce organic acids that generate the colored zones, the colored zones increase in size and begin to merge with the colored zones of surrounding nearby colonies. When enough growing, acidproducing colonies are present, the medium may eventually completely change color from red to yellow. When the color of the medium completely changes from red to yellow after about 24 hours, it is possible detect a second color change using another indicator in the medium.

SUMMARY OF THE INVENTION

This invention overcomes the deficiencies of current products and processes referred to above by providing products and processes which allow detection and enumeration of Enterobacteriacea as well as controlling the diffusion of colored indicator zones through the medium caused by a pH indicator which changes color in response to organic acids produced by growing Enterobacteriaceae colonies.

One embodiment of the present invention is a bacterial culture medium which facilitates the detection and enumeration of Enterobacteriaceae growing in the medium. The medium includes selected amounts of glucose, a pH indicator and buffer to prevent colored indicator zones from excessively diffusing in the medium. When used, the amounts of glucose, pH indicator and buffer are selected to provided optimum growth of microorganisms in the colony without enabling the colored zone around growing colonies associated with the pH indicator to diffuse through the medium.

Preferred media for use in the present invention depend on the diluent which is used to prepare the initial sample. When the diluent which is used to prepare the sample is an aqueous diluent of about 0.6 mMol potassium phosphate (commonly referred to as Butterfields Standard Methods Buffer), a preferred gelatin peptone culture medium includes about 7–14 g/l, 6–9 g/l yeast extract, 5–20 g/l glucose, 5–15 g/l sodium chloride, 2.7–3.15 g/l bile salts, 5–13 g/l guar gum, 0.6–2 g/l monobasic potassium phosphate, 1.8–6 g/l dibasic potassium phosphate, and 0.2–0.8 g/l pH indicato includes about 14 g/l gelatin peptone, 6 g/l yeast extract, 20 g/l glucose, 10 g/l sodium chloride, 3 g/l bile salts, 11 g/l guar gum, 2 gl monobasic potassium phosphate, 6 g/l dibasic potassium phosphate, and 0.4 g/l pH indicator.

Alternatively, when the diluent which is used to prepare the sample is an aqueous diluent consisting essentially of about 0.1 wt/vol % casein peptone and 0.85 wt/vol % sodium chloride (commonly referred to as peptone salt buffer), a preferred culture medium includes about 7–14 g/l gelatin peptone, 6–9 g/l yeast extract, 5–20 g/l glucose, 2.7–3.15 g/l bile salts, 5–13 g/l guar gum, 0.2–1 g/l monobasic potassium phosphate, 0.6–3 gl dibasic potassium phosphate, and 0.2–0.8 g/l pH indicator. A particular preferred culture medium includes about 14 g/l gelatin peptone, 6 g/l yeast extract, 20 g/l glucose, 3 g/l bile salts, 11 g/l guar gum, 0.4 g/l monobasic potassium phosphate, 1.2 g/l dibasic potassium phosphate, and 0.4 g/l pH indicator.

After the sample is diluted, the pH of the diluent is adjusted to about 6.5–7.5, preferably about 7.0 by the addition of 1N aqueous sodium hydroxide.

Those of ordinary skill in the art will recognize that the difference between the preferred culture medium for use with Butterfelds Standard Methods Buffer and the preferred culture medium for use with casein peptone diluent is the difference in salt concentration. Other diluents may require similar adjustment or modification to provide a desired salt concentration for use in the culture medium. In general, the salt concentration of a culture medium of this invention should be in the range of about 10–25 mMol, preferably.

Preferred pH indicators for use in this invention include known, commercially available acidbase indicators which are commonly classified as azobenzene, sulfonphthalein, or anthroquinone dyes. Representative pH indicators from the listed classes of indicators include methyl red (an azobenzene indicator), bromocresol purple, chlorophenol red, bromthymol blue, bromcresol blue (all sulfonphthalein indicators), and alizarin red s monohydrate 3,4-dihydroxy-9,10-dioxo-2-anthracenesulfonic acid, sodium salt (anthroquinone). A particularly preferred pH indicator is chlorophenol red.

Another embodiment of the present invention is method of detecting and enumerating Entrobacteriaceae in a sample. This method includes the steps of adding an aliquot of a sample in an aqueous diluent to a culture medium containing selected amounts of glucose, pH indicator and buffer to prevent colored indicator zones from excessively diffusing in the medium, adjusting the pH of the diluent to about 6.5–7.5; growing Enterobacteriaceae in the presence of the culture medium; and detecting the color change of the pH indicator in the medium. When this method is used, a preferred device is a thin fdm culture plate device having a selfsupporting, waterproof substrate, a foam spacer and a transparent cover sheet. A preferred device includes a self-supporting, waterproof substrate coated with a dry medium, a foam spacer and a transparent cover sheet. The self-supporting, waterproof substrate is coated with the medium of this invention in order to prevent colored indicator zones from excessively diffusing in the medium. In addition, the cover sheet of the thin fdm device is generally coated with additional gums andor gelling agents as well as a second indicator such as triphenyltetrazolium chloride. Preferably the cover sheet contains about 0.02 mg/in$^2$ triphenyltetrazolium chloride.

DETAILED DESCRIPTION

This invention provides products and processes which may be used to detect the presence of Enterobacteriaceae in a sample, preferably in a food sample. Although a variety of products and processes may be used to detect Enterobacteriaceae, the medium and related device of the present invention greatly simplify the detection and enumeration of Enterobacteriaceae in a sample.

Specifically, both detection and enumeration of Enterobacteriaceae in most samples has been problematic for a variety of reasons. In most cases, when these bacteria are present in a sample they have been stressed and are not growing at an optimal level. In order to provide for optimal growth (and thus provide the earliest detection) the stressed bacteria must be provided a period of time to recover from induced stress. The present invention provides a medium which is believed to afford rapid recovery of Enterobacteriaceae. The medium includes known reagents and nutrients which are commercially available. These reagents and nutrients include gelatin peptone, yeast extract, glucose, sodium chloride, bile salts and buffers which are available from Acumedia, Inc., Baltimore, Md. and Sigma Chemical Company, St. Louis, Mo. The medium also contains guar gum which is commercially available from Rhone-Poulenc, Inc., Kreuzlinger, Switzerland. Tne indicators which are used in the media are also commercially available from Aldrich Chemical Company, Inc., Milwaukee, Wis., and triphenyltetrazolium chloride is commercially available from AMRESCO, Solon, Ohio. The preferred reagents and materials are weighed and mixed using conventional aseptic procedures.

The present culture medium includes at least one acidbase or pH indicator. Suitable indicators will change color in the presence of acid. As a bacterial colony grows, the colony produces metabolic organic acids which react with the indicator and produce zones or areas surrounding the colony which are a different color than the medium. For example, chlorophenol red provides a red colored medium which changes to a yellow color in the presence of acid. Suitable pH indicators are commonly classified as azobenzene, sulfonphthalein, or anthroquinone dyes. Representative pH indicators from the listed classes of indicators include methyl red (an azobenzene indicator), bromocresol purple, chlorophenol red, bromthymol blue, bromcresol blue (all sulfonphthalein indicators), and alizarin red s monohydrate 3,4-dihydroxy-9,10-dioxo-2-anthracensulfonic acid, sodium salt (anthroquinone).

Figure 1:
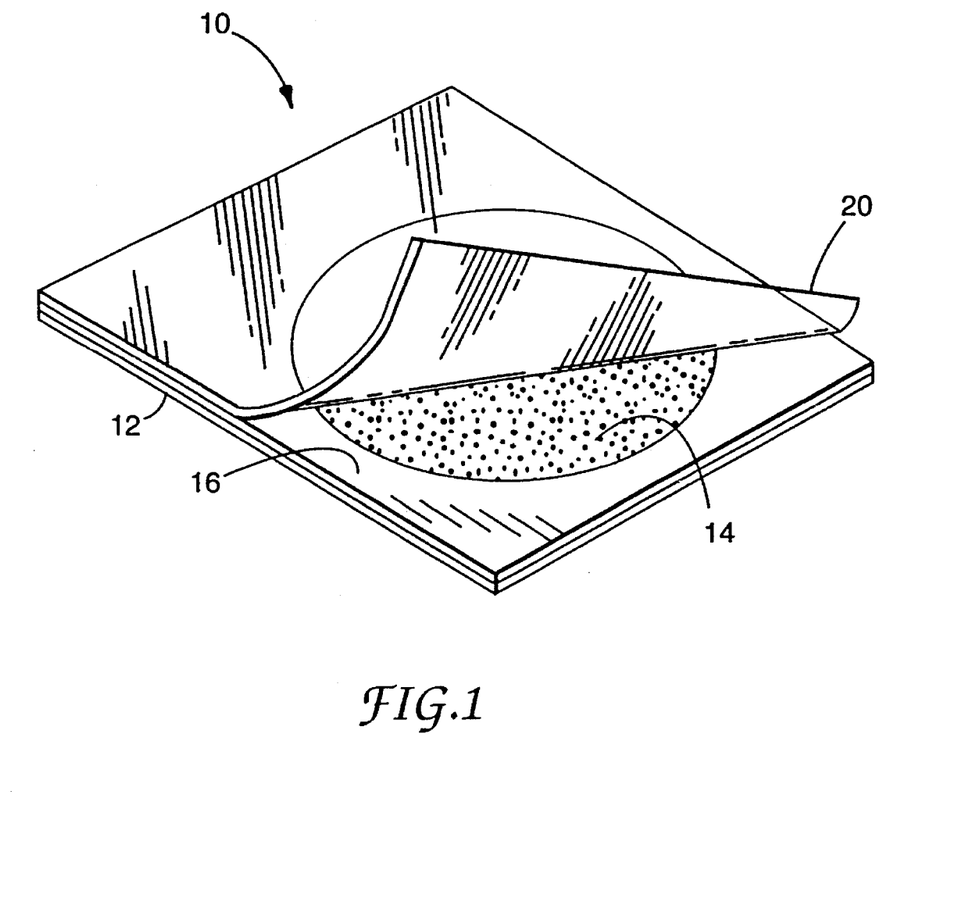
FIG. 1 is an illustration of a thin film culture plate device containing the culture medium of the present invention.

FIG. 1 illustrates a thin film, dry culture medium device suitable for use with the media of the present invention. Briefly, the device is described in U.S. Pat. Nos. 4,565,783, 5,089,413 and 5,232,838 which are incorporated by reference in this application for the purposes of describing the processes of making and using these types of devices.

The thin film culture device 10 includes a body member having a self-supporting, waterproof substrate 12. Substrate 12 is preferably a relatively stiff material made of a waterproof material that does not absorb water such as polyester, polypropylene, or polystyrene. Other suitable waterproof materials include substrates such as paper containing a waterproof polyethylene coating.

The upper surface of substrate 12 is coated with a layer of culture media 14 which is then dried to provide a dry medium on substrate 12. Alternatively, a layer of adhesive may be coated on substrate 12 of adhesive which serves to hold a culture medium which may be applied as a powder. The adhesive should be sufficiently transparent when hydrated to allow viewing of bacterial colonies growing on the surface of the substrate through the coated substrate. The adhesive should also be coated on the substrate in a thickness which allows the substrate to be uniformly coated with dry culture medium without completely embedding the media in the adhesive.

If the liquid culture medium of this invention is to be used in a dry form or as a dry powder, the reagents, nutrients, gums and pH indicator are added as a liquid to the substrate and then dried. The culture medium of this invention may be readily dried by heating liquid medium in an oven at about 220° F. until essentially all of the water in the liquid has evaporated. If the medium is heated after the water has evaporated, however, the medium begins to degrade.

A foam spacer 16 having a circular opening in the foam is adhered to the medium coated surface of substrate 12. The foam spacer which covers the periphery of substrate 12 defines the area which is to be inoculated with a sample and serves to prevent the sample from leaking from the substrate. In an alternate embodiment, a device may not include a samplecontaining foam layer. In this device, the amount of sample is contained on the substrate by the components of the medium alone.

A cover sheet 20 is attached to one edge of an upper surface of the foam spacer 16. Cover sheet 20 is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxiallyoriented polypropylene. The cover sheet is typically coated with additional gums and a second indicator.

In use, a predetermined amount of inoculum, typically about one milliliter of inoculum, is added to the device illustrated in FIG. 1 by pulling back cover sheet 20 and adding an aqueous test sample or water to the middle of substrate 12. Cover sheet 20 is then replaced over substrate 12 and the inoculum is evenly spread on the substrate. A convenient tool to do this is a weighted circular template which also is used to confine the inoculum to a specific area of substrate 12. As the inoculum contacts and is spread on substrate 12, the culture medium on substrate 12 hydrates to form a growthsupporting nutrient gel. The inoculated device is then incubated for a predetermined time after which the number of bacterial colonies growing on the substrate may be counted through the transparent cover sheet 20.

When the culture medium of this invention is in a dry state on a thin film and then covered with a foam spacer the concentration of components in the media which actually come in contact with the sample are one-half (0.5) the concentration of the components in the liquid medium before it is dried on the substrate.

Detection of Enterobacteriaceae in the culture medium may be done visually or done using an instrument. Suitable instruments are described in the related U.S. patent applications Ser. No. 08/272,996 filed Jul. 14, 1994 now U.S. Pat. No. 5,403,722 and Ser. No. 08/168,681 filed Dec. 17, 1993 pending.

Although the use of the culture medium of this invention on a thin film device is described above, those of ordinary skill in the art will recognize that the culture media may be used in other culturing devices which are known in the art. For example, the culture medium may be used as a broth and used to grow bacteria in suspension or the culture media may be use to grow bacteria on known agar plates.

The ability to detect the presence of enumerate microorganisms is very valuable in many circumstances. For example, detection and enumeration of Enterobacteriaceae is important in the food industry. Although the food industry would clearly benefit by determining EnterobacteriaLea. contamination, other industries including cosmetics, water testing, and pharmaceuticals, would also welcome the opportunity to readily detect these bacteria more.

The following examples are intended to provide further details and embodiments related to the practice of the present invention. These examples are provided for illustrative purposes and should not be construed to limit the scope of the present invention which is defined in the appended claims.

EXAMPLE 1

Growth of Enterobacteriaceae in Medium
Containing Different Glucose Concentrations This example illustrates that a preferred culture medium of this invention (Enterobacteriaceae growth medium, EGM) may be used to grow Enterobacteriaceae in a thin film, dry culture medium device. The medium used in this example contained 14 gl gelatin peptone (Accumedia), 6 g/l yeast extract (Aecumedia), 10 g/l sodium chloride (Sigma), 3 gl bile salts (Accumedia), and 11 g/l guar gum (Rhone-Poulenc). The glucose and pH indicator were used a varying concentrations as listed in Table 1, below. The listed components were commercially available from the sources listed above.

Briefly, the different media were prepared by dissolving the nutrients, salts and gums in one liter of aleionized water. This mixture was then brought to a boil, cooled to about room temperature and then glucose and pH indicator were added.

Two representative Enterobacteriaceae species, *Escherichia coli* 149 (ATCC Accession Number 55535) and *Serratia liquefaciens* C1 (quality control isolates used by 3M Microbiology Products Laboratory, maintained as frozen samples by 3M, St. Paul, Minn.), were initially grown for 18–24 hours in trypticase soy broth (Difco Laboratories, Inc., Detroit, Mich.) at 35° C. These growing cultures contained about $10^8$–$10^9$ bacteria/ml and were then serially diluted about $10^6$–$10^7$ fold in Butterfields Standard Methods Buffer (SMB, Fisher Scientific, Minneapolis, Minn.) in order to provide samples which would contain about 20–50 colony-forming units per plate. Those of ordinary skill will recognize that equivalent strains or species of bacteria are commercially available or may be isolated using well known methods or processes.

Thin film, dry culture medium devices were prepared by as follows. A layer of EG was forced through a small orifice in order to cover a 7.5 mil (0.19 mm) (need length and width) polyester substrate film (Imperial Chemical industries, Wilmington, Del.) at room temperature. The covered polyester film was then dried for between about 1–20 minutes at about 200°–250° F. An 18 mil (0.46 mm) styrofoam spacer sheet was cut to cover the polyester film and a circular opening was cut in the styrofoam spacer. One surface of the styrofoam spacer was coated with an isooctyl acrylate/acrylic acid adhesive (98 wt % isooctyl acrylate copolymerized with 2 wt % acrylic acid) and the styrofoam sheet was adhered to the coated surface of the polyester film. The opening in the styrofoam spacer provide a well having a diameter of about 2 inches (about 5 cm).

A transparent polypropylene film was cut to cover the polyesterstyrofoam laminated film. One surface of the polypropylene film (1.6 mil (0.041 mm), 3M, St. Paul, Minn.

was coated with an isooctyl acrylateacrylic acid adhesive (98 wt % isooctyl acrylate copolymerized with 2 wt % acrylic acid) and then coated with a layer of guar gum (RhonePoulenc, Inc. Kreuzlinger, Switzerland) and triphenyl tetrazolium chloride. A layer of double-sided adhesive coated tape (3M, St. Paul, Minn.) was placed on one exposed edge of the styrofoam spacer and the gum-containing surface of the polypropylene film was adhered to the styrofoam spacer along one edge.

The cultured aliquots (one ml) were placed in the opening of the styrofoam spacer, the polypropylene film was used to cover the inoculum, and the thin film device was incubated for 24 hours at 35° C.

After incubation for 24 hours, thin film plates were evaluated for the presence of acid zones which were identified as yellow areas on the red background of the plate. Zone sizes were measured and are recorded in Table 1.

The data listed in Table 1 below indicate that EGM was selective for growing EnterobacteriaCeae at various concentrations of both glucose and pH indicator to yield discrete, distinguishable colored zones around growing bacterial colonies.

TABLE 1

| Glucose Conc. (% wt/v) | pH Indicator | Conc (mM) | Read-out (24 h) |
|---|---|---|---|
| 5 | Phenol Red | 1 | 4+/4+ |
| 2.5 | Phenol Red | 1 | 4+/4+ |
| 1 | Phenol Red | 1 | 4+/4+ |
| 0.5 | Phenol Red | 1 | 4+/4+ |
| 0.25 | Phenol Red | 1 | 4+/2+ |
| 0.1 | Phenol Red | 1 | 2+/0 |
| 5 | Phenol Red | 0.5 | 4+/4+ |
| 2.5 | Phenol Red | 0.5 | 4+14+ |
| 1 | Phenol Red | 0.5 | 4+/4+ |
| 0.5 | Phenol Red | 0.5 | 4+/4+ |
| 0.25 | Phenol Red | 0.5 | 4+/2+ |
| 0.1 | Phenol Red | 0.5 | 2+/0 |
| 5 | Phenol Red | 0.25 | 4+/4+ |
| 2.5 | Phenol Red | 0.25 | 4+/4+ |
| 1 | Phenol Red | 0.25 | 4+/4+ |
| 0.5 | Phenol Red | 0.25 | 4+/4+ |
| 0.25 | Phenol Red | 0.25 | 4+/2+ |
| 0.1 | Phenol Red | 0.25 | 2+/0 |
| 5 | Phenol Red | 0.125 | 4+/4+ |
| 2.5 | Phenol Red | 0.125 | 3+/1+ |
| 1 | Phenol Red | 0.125 | 3+/+− |
| 0.5 | Phenol Red | 0.125 | 3+/+− |
| 0.25 | Phenol Red | 0.125 | 2+/0 |
| 0.1 | Phenol Red | 0.125 | 0/0 |
| 5 | Bromocresol Purple | 1 | 4+/4+ |
| 2.5 | Bromocresol Purple | 1 | 4+/4+ |
| 1 | Bromocresol Purple | 1 | 3+/3+ |
| 0.5 | Bromocresol Purple | 1 | 3+/2+ |
| 0.25 | Bromocresol Purple | 1 | 3+/2+ |
| 0.1 | Bromocresol Purple | 1 | 1+/0 |
| 5 | Bromocresol Purple | 0.5 | 4+/4+ |
| 2.5 | Bromocresol Purple | 0.5 | 4+/4+ |
| 1 | Bromocresol Purple | 0.5 | 3+/3+ |
| 0.5 | Bromocresol Purple | 0.5 | 3+/2+ |
| 0.25 | Bromocresol Purple | 0.5 | 3+/2+ |
| 0.1 | Bromocresol Purple | 0.5 | 1+/0 |
| 5 | Bromocresol Purple | 0.25 | 4+/4+ |
| 2.5 | Bromocresol Purple | 0.25 | 4+4+ |
| 1 | Bromocresol Purple | 0.25 | 3+/3+ |
| 0.5 | Bromocresol Purple | 0.25 | 3+/2+ |
| 0.25 | Bromocresol Purple | 0.25 | 3+2+ |
| 0.1 | Bromocresol Purple | 0.25 | 1+/0 |
| 5 | Bromocresol Purple | 0.125 | 4+/4+ |
| 2.5 | Bromocresol Purple | 0.125 | 3+/+− |
| 1 | Bromocresol Purple | 0.125 | 2+/+− |
| 0.5 | Bromocresol Purple | 0.125 | 3+/0 |
| 0.25 | Bromocresol Purple | 0.125 | 2+/0 |
| 0.1 | Bromocresol Purple | 0.125 | 0/0 |

TABLE 1-continued

| Glucose Conc. (% wt/v) | pH Indicator | Conc (mM) | Read-out (24 h) |
|---|---|---|---|
| 5 | Chlorophenol Red | 1 | 3+/3+ |
| 2.5 | Chlorophenol Red | 1 | 3+/3+ |
| 1 | Chlorophenol Red | 1 | 3+/2+ |
| 0.5 | Chlorophenol Red | 1 | 3+/2+ |
| 0.25 | Chlorophenol Red | 1 | 3+/1+ |
| 0.1 | Chlorophenol Red | 1 | 1+/0 |
| 5 | Chlorophenol Red | 0.5 | 3+/3+ |
| 2.5 | Chlorophenol Red | 0.5 | 3+/3+ |
| 1 | Chlorophenol Red | 0.5 | 3+/2+ |
| 0.5 | Chlorophenol Red | 0.5 | 3+/2+ |
| 0.25 | Chlorophenol Red | 0.5 | 3+/1+ |
| 0.1 | Chlorophenol Red | 0.5 | 1+/0 |
| 5 | Chlorophenol Red | 0.25 | 3+/3+ |
| 2.5 | Chlorophenol Red | 0.25 | 3+/3+ |
| 1 | Chlorophenol Red | 0.25 | 3+/2+ |
| 0.5 | Chlorophenol Red | 0.25 | 3+/2+ |
| 0.25 | Chlorophenol Red | 0.25 | 3+/1+ |
| 0.1 | Chlorophenol Red | 0.25 | 1+/0 |
| 5 | Chlorophenol Red | 0.125 | 3+/3+ |
| 2.5 | Chlorophenol Red | 0.125 | 3+/+− |
| 1 | Chlorophenol Red | 0.125 | 2+/+− |
| 0.5 | Chlorophenol Red | 0.125 | 3+/0 |
| 0.25 | Chlorophenol Red | 0.125 | 2+/0 |
| 0.1 | Chlorophenol Red | 0.125 | 0/0 |
| 5 | Methyl Red | 1 | 3+/3+ |
| 2.5 | Methyl Red | 1 | 3+/2+ |
| 1 | Methyl Red | 1 | 3+/2+ |
| 0.5 | Methyl Red | 1 | 3+/2+ |
| 0.25 | Methyl Red | 1 | 3+/1+ |
| 0.1 | Methyl Red | 1 | 1+/0 |
| 5 | Methyl Red | 0.5 | 3+/2+ |
| 2.5 | Methyl Red | 0.5 | 3+/2+ |
| 1 | Methyl Red | 0.5 | 3+/2+ |
| 0.5 | Methyl Red | 0.5 | 3+/2+ |
| 0.25 | Methyl Red | 0.5 | 3+/1+ |
| 0.1 | Methyl Red | 0.5 | 1+/0 |
| 5 | Methyl Red | 0.25 | 3+/2+ |
| 2.5 | Methyl Red | 0.25 | 3+/2+ |
| 1 | Methyl Red | 0.25 | 3+/2+ |
| 5 | Methyl Red | 0.25 | 3+/2+ |
| 0.2 | Methyl Red | 0.25 | 3+/1+ |
| 0.1 | Methyl Red | 0.25 | 1+/0 |
| 5 | Methyl Red | 0.125 | 3+/2+ |
| 2.5 | Methyl Red | 0.125 | 3+/+− |
| 1 | Methyl Red | 0.125 | 2+/+− |
| 0.5 | Methyl Red | 0.125 | 3+/0 |
| 0.25 | Methyl Red | 0.125 | 2+/0 |
| 0.1 | Methyl Red | 0.125 | 0/0 |

0 = no acid
+− = <1.5 mm a.z.
1+ = 1.5–2.0 mm a.z.
2+ = 2.0–3.0 mm a.z.
3+ = 3.0–4.0 mm a.z.
4+ = >/= 4.0 mm a.z.

EXAMPLE 2

Growth Of Enterobacteria in Medium Containing Different Buffer Concentrations.

This example demonstrates that the concentration of buffer may be used to control the diffusion of a pH indicator in a medium selected to grow Enterobacteriaceae. The medium used in this experiment was prepared as described in Example 1 except that the concentration of glucose was fixed at 10 g/l while concentrations of different buffers and pH indicators were changed as listed in Table 2. Buffers listed in Table 2 were prepared according to accepted procedures. When two buffers were used the final concentration listed in Table 2 is made of onehalf of each of the listed buffers.

The data listed in Table 2 below indicate that EGM was selective for growing Enterobacteriaceae. Several buffers and pH indicators provided the desired effect of reducing the size of colored zones around growing bacterial colonies.

TABLE 2

| Buffer Species | Molarity (mM) | Dye Species | Conc (mM) | Read-out (24 h) |
|---|---|---|---|---|
| KHP04 | 100 | Methyl Red | 1 | 1+/0 |
| KHP04 | 50 | Methyl Red | 1 | 1+/0 |
| KHP04 | 25 | Methyl Red | 1 | 2+/1+ |
| KHP04 | 12.5 | Methyl Red | 1 | 2+/1+ |
| KHP04 | 0 | Methyl Red | 1 | 3+/2+ |
| Carbonate | 100 | Methyl Red | 0 | 1+/0 |
| Carbonate | 50 | Methyl Red | 1 | 1+/+− |
| Carbonate | 25 | Methyl Red | 1 | 2+/2+ |
| Carbonate | 12.5 | Methyl Red | 1 | 3+/3+ |
| Carbonate | 0 | Methyl Red | 1 | 3+/3+ |
| Citrate/Acetate | 100 | Methyl Red | 1 | 1+/0 |
| Citrate/Acetate | 50 | Methyl Red | 1 | 1+/0 |
| Citrate/Acetate | 25 | Methyl Red | 1 | 2+/2+ |
| Citrate/Acetate | 12.5 | Methyl Red | 1 | 2+/2+ |
| Citrate/Acetate | 0 | Methyl Red | 1 | 3+/3+ |
| Citrate/Phosphate | 100 | Methyl Red | 1 | 1+/0 |
| Citrate/Phosphate | 50 | Methyl Red | 0 | 1+/0 |
| Citrate/Phosphate | 25 | Methyl Red | 1 | 2+/2+ |
| Citrate/Phosphate | 12.5 | Methyl Red | 1 | 2+2+ |
| Citrate/Phosphate | 0 | Methyl Red | 1 | 3+/3+ |
| KHP04 | 100 | Bromocresol Purple | 0.5 | 1+/0 |
| KHP04 | 50 | Bromocresol Purple | 0.5 | 1+/0 |
| KHP04 | 25 | Bromocresol Purple | 0.5 | 2+/2+ |
| KHP04 | 12.5 | Bromocresol Purple | 0.5 | 2+/2+ |
| KHP04 | 0 | Bromocresol Purple | 0.5 | 3+/2+ |
| Carbonate | 100 | Bromocresol Purple | 0.5 | 1+/0 |
| Carbonate | 50 | Bromocresol Purple | 0.5 | 1+/0 |
| Carbonate | 25 | Bromocresol Purple | 0.5 | 2+/2+ |
| Carbonate | 12.5 | Bromocresol Purple | 0.5 | 3+/3+ |
| Carbonate | 0 | Bromocresol Purple | 0.5 | 3+/3+ |
| Citrate/Acetate | 100 | Bromocresol Purple | 0.5 | 1+/0 |
| Citrate/Acetate | 50 | Bromocresol Purple | 0.5 | 1+/1+ |
| Citrate/Acetate | 25 | Bromocresol Purple | 0.5 | 2+/2+ |
| Citrate/Acetate | 12.5 | Bromocresol Purple | 0.5 | 3+/3+ |
| Citrate/Acetate | 0 | Bromocresol Purple | 0.5 | 3+/3+ |
| Citrate/Phosphate | 100 | Bromocresol Purple | 0.5 | 1+/0 |
| Citrate/Phosphate | 50 | Bromocresol Purple | 0.5 | 2+/0 |
| Citrate/Phosphate | 25 | Bromocresol Purple | 0.5 | 2+/2+ |
| Citrate/Phosphate | 12.5 | Bromocresol Purple | 0.5 | 3+/3+ |
| Citrate/Phosphate | 0 | Bromocresol Purple | 0.5 | 3+/3+ |
| KHP04 | 100 | Chlorophenol Red | 0.5 | 1+/0 |
| KHP04 | 50 | Chlorophenol Red | 0.5 | 1+/0 |
| KHP04 | 25 | Chlorophenol Red | 0.5 | 2+/1+ |
| KHP04 | 12.5 | Chlorophenol Red | 0.5 | 2+/1+ |
| KHP04 | 0 | Chlorophenol Red | 0.5 | 3+/2+ |
| Carbonate | 100 | Chlorophenol Red | 0.5 | 1+/0 |
| Carbonate | 50 | Chlorophenol Red | 0.5 | 1+/0 |
| Carbonate | 25 | Chlorophenol Red | 0.5 | 2+/2+ |
| Carbonate | 12.5 | Chlorophenol Red | 0.5 | 3+/3+ |
| Carbonate | 0 | Chlorophenol Red | 0.5 | 3+/3+ |
| Citrate/Acetate | 100 | Chlorophenol Red | 0.5 | 1+/0 |
| Citrate/Acetate | 50 | Chlorophenol Red | 0.5 | 1+/+− |
| Citrate/Acetate | 25 | Chlorophenol Red | 0.5 | 2+/2+ |
| Citrate/Acetate | 12.5 | Chlorophenol Red | 0.5 | 3+/2+ |
| Citrate/Acetate | 0 | Chlorophenol Red | 0.5 | 3+/3+ |
| Citrate/Phosphate | 100 | Chlorophenol Red | 0.5 | 1+/0 |
| Citrate/Phosphate | 50 | Chlorophenol Red | 0.5 | 2+/0 |
| Citrate/Phosphate | 25 | Chlorophenol Red | 0.5 | 2+/2+ |
| Citrate/Phosphate | 12.5 | Chlorophenol Red | 0.5 | 3+/3+ |
| Citrate/Phosphate | 0 | Chlorophenol Red | 0.5 | 3+/3+ |
| KHP04 | 25 | Alizarin Red S Monohydrate | 0.5 | 2+/2+ |

0 = no acid zone
plus minus = <1.5 mm a.z.
1+ = 1.5–2.0 mm a.z.
2+ = 2.0–3.0 mm a.z.
3+ = 3.0–4.0 mm a.z.
4+ = >/= 4.0 mm a.z.

We claim:

1. A bacterial culture medium comprising glucose and a pH indicatorbuffer system to detect and enumerate EntCrobacteriaceae growing in the medium wherein the medium contains selected amounts of glucose, pH indicator and buffer to prevent colored indicator zones from excessively diffusing in the medium.

2. The culture medium of claim 1 wherein a sample containing Enterobacteriaceae is added to the culture medium in an aqueous diluent consisting essentially of about 0.6 mMol sodium phosphate.

3. The culture medium of claim 2 comprising about 7–14 g/l gelatin peptone, 6–9 g/l yeast extract, 5–20 g/l glucose, 5–15 g/l sodium chloride, 2.7–3.15 g/l bile salts, 5–13 g/l guar gum, 0.6–2 g/l monobasic potassium phosphate, 1.8–6 g/l dibasic potassium phosphate, and 0.2–0.8 g/l pH indicator.

4. The culture medium of claim 2 containing about 14 gl gelatin peptone, 6 g/l yeast extract, 20 g/l glucose, 10 g/l sodium chloride, 3 g/l bile salts, 11 g/l guar gum, 2 g/l monobasic potassium phosphate, 6 g/l dibasic potassium phosphate, and 0.4 g/l pH indicator.

5. The culture medium of claim 1 wherein a sample containing Enterobacteriaceae is added to the culture medium in an aqueous diluent consisting essentially of about 0.1 wt/vol % casein peptone and 0.85 wt/vol % sodium chloride.

6. The culture medium of claim 5 comprising about 7–14 g/l gelatin peptone, 6–9 g/l yeast extract, 5–20 g/l glucose, 2.7–3.15 g/l bile salts, 5–13 g/l guar gum, 0.2–1 g/l monobasic potassium phosphate, 0.6–3 g/l dibasic potassium phosphate, and 0.2–0.8 g/l pH indicator.

7. The culture medium of claim 5 containing about 14 g/l gelatin peptone, 6 g/l yeast extract, 20 g/l glucose, 3 g/l bile salts, 11 g/l guar gum, 0.4 g/l monobasic potassium phosphate, 1.2 g/l dibasic potassium phosphate, and 0.4 g/l pH indicator.

8. The culture medium of claim 1 wherein pH indicator is selected from the group consisting of azobenzene, sulfonphthalein and anthroquinone pH indicators.

9. The culture medium of claim 8 wherein the pH indicator is selected from the group consisting of methyl red, bromocresol purple, chlorophenol red, bromthymol blue, bromcresol blue, and 3,4-dihydroxy-9, 10-dioxo-2-anthracenesulfonic acid, sodium salt.

10. The culture medium of claim 9 wherein the pH indicator is chlorophenol red.

11. A method of detecting and enumerating Enterobactriaceae in a sample comprising the steps of adding an aliquot of a sample in an aqueous diluent to a culture medium containing selected amounts of glucose, pH indicator and buffer to prevent colored indicator zones from excessively diffusing in the medium, adjusting the pH of the aliquot to about 6.57–7.5; growing Enterobacteriaceae in the presence of the culture medium; and detecting the color change of the pH indicator in the medium.

12. The method of claim 11 wherein the sample is added to a thin film containing the medium using a device having a self-supporting, waterproof substrate, a foam spacer and a transparent cover sheet, wherein a culture media is coated on the waterproof substrate and then dried.

13. A device to detect and enumerate Enterobacteriaceae in a sample consisting essentially of a coated self-supporting, waterproof substrate, a foam spacer and a transparent cover sheet, wherein a culture medium containing selected amounts of glucose, pH indicator and buffer to prevent colored indicator zones from excessively diffusing in the medium is coated on the self-supporting, waterproof substrate.

* * * * *

UNITED STATES PATENT AND TRADEMARK OFFICE
CERTIFICATE OF CORRECTION

PATENT NO.    : 5,601,998
DATED         : February 11, 1997
INVENTOR(S)   : Patrick A. Mach, Peter D. Wickert, and Carl A. Adams It is certified that error appears in the above-indentified patent and that said Letters Patent is hereby corrected as shown below:

Title Page: In the Subheading "Inventors" after "Patrick A. Mach' insert --Shorewood, Minn.;-- after Peter D. Wickert" insert --St. Paul, Minn.;-- after Carl A. Adams" insert --Apple Valley, Minn.;-- and delete "all of P.O. Box 33427, St. Paul, Minn. 55133-3427.

After Subheading "Inventors" and before Subheading "Appl. No.:" insert --Assignee: Minnesota Mining and Manufacturing Company, St. Paul, Minnesota--.

After Subheading "Assistant Examiner — Louise N. Leary" and before Subheading "ABSTRACT" insert --Attorney, Agent, or Firm — Gary L. Griswold; Walter N. Kim; James A. Rogers--.

Column 1, Line 14: Delete "EnterobacteriaCeae" and insert in place thereof --Enterobacteriaceae--.

Column 1, Line 34: Delete "Enterobactefi.aceae" and insert in place thereof --Enterobacteriaceae--.

Column 1, Line 66: Delete "mediumpetri/" and insert in place thereof --medium/petri--.

Column 2, Line 28: Delete "acidproducing" and insert in place thereof --acid-producing--.

Column 2, Line 31: After the word "possible" and before the word "detect" insert --to--.

Column 2, Line 63: Delete "indicato" and insert in place thereof --indicator.--.

Column 2, Line 64: Before the word "includes" insert --A particular preferred culture medium--.

Column 3, Line 27: Delete "acidbase" and insert in place thereof --acid-base--.

Column 3, line 47 delete "fdm" insert --film--.

UNITED STATES PATENT AND TRADEMARK OFFICE
CERTIFICATE OF CORRECTION

PATENT NO. : 5,601,998
DATED : February 11, 1997
INVENTOR(S) : Patrick A. Mach, Peter D. Wickert, and Carl A. Adams It is certified that error appears in the above-indentified patent and that said Letters Patent is hereby corrected as shown below:

Column 8, Line 38: Delete "0.2" and insert in place thereof --0.25--.

Column 8, Line 66: Delete "onehalf" and insert in place thereof --one-half--.

Column 10, Line 31: Claim 1: Delete "indicatorbuffer" and insert in place thereof --indicator/buffer--.

Column 10, Line 31: Claim 1: Delete "EntCrobacteriaceae" and insert in place thereof --Enterobacteriaceae--.

Column 10, Line 45: Claim 4: Delete "14 gl" and insert in place thereof --14 g/l--.

Column 11, Line 8: Claim 11: Delete "Enterobactriaceae" and insert in place thereof --Enterobacteriaceae--.

Column 11, Line 14: Claim 11: Delete "6.57-7.5" and insert in place thereof --6.5-7.5--.

UNITED STATES PATENT AND TRADEMARK OFFICE
CERTIFICATE OF CORRECTION

PATENT NO. : 5,601,998
DATED : February 11, 1997
INVENTOR(S) : Patrick A. Mach, Peter D. Wickert, and Carl A. Adams It is certified that error appears in the above-indentified patent and that said Letters Patent is hereby corrected as shown below:

Column 3, Line 48: Delete "selfsupporting" and insert in place thereof --self-supporting--.

Column 3, Line 56: Delete "andor" and insert in place thereof --and/or--.

Column 4, Line 29: Delete "acidbase" and insert in place thereof --acid/base--.

Column 5, Line 18: Delete "samplecontaining" and insert in place thereof --sample-containing--.

Column 5, Line 28: Delete "biaxiallyoriented" and insert in place thereof --biaxially-oriented--.

Column 5, Line 41: Delete "growthsupporting" and insert in place thereof --growth-supporting--.

Column 5, Line 64: Delete "use" and insert in place thereof --used--.

Column 6, Line 2: Delete "EnterobacteriaLea." and insert in place thereof --Enterobacteriaceae--.

Column 6, Line 22: Delete "14 gl" and insert in place thereof --14 g/l--.

Column 6, Line 24: Delete "3 gl" and insert in place thereof --3 g/l--.

Column 6, Line 30: Delete "aleionized" and insert in place thereof --deionized--.

Column 6, Line 66: Delete "polyesterstyrofoam" and insert in place thereof --polyester/styrofoam--.

Column 7, Line 1: Delete "acrylateacrylic" and insert in place thereof --acrylate/acrylic--.

Column 7, Line 19: Delete "EnterobacteriaCeae" and insert in place thereof --Enterobacteriaceae--.

Column 7, Line 34: Delete "4+14+" and insert in place thereof --4+/4+--.

Signed and Sealed this

Twenty-fifth Day of August, 1998

Attest:

Attesting Officer

BRUCE LEHMAN

Commissioner of Patents and Trademarks